US012735467B2

(12) United States Patent
Han et al.

(10) Patent No.: US 12,735,467 B2
(45) Date of Patent: Sep. 15, 2026

(54) POLYPEPTIDE DERIVATIVE HAVING DUAL RECEPTOR AGONISTIC ACTION AND USE THEREOF

(71) Applicant: TIANJIN INSTITUTE OF PHARMACEUTICAL RESEARCH CO., LTD., Tianjin (CN)

(72) Inventors: Yingmei Han, Tianjin (CN); Wei Liu, Tianjin (CN); Bingni Liu, Tianjin (CN); Weiling Kong, Tianjin (CN); Naxia Zhao, Tianjin (CN); Guangping Xia, Tianjin (CN); Qian Shang, Tianjin (CN); Jing Jin, Tianjin (CN); Xiaohua Kong, Tianjin (CN); Yuquan Li, Tianjin (CN); Songhui Wang, Tianjin (CN)

(73) Assignee: TIANJIN INSTITUTE OF PHARMACEUTICAL RESEARCH CO., LTD., Tianjin (CN)

( * ) Notice: Subject to any disclaimer, the term of this patent is extended or adjusted under 35 U.S.C. 154(b) by 905 days.

(21) Appl. No.: 17/923,936

(22) PCT Filed: May 8, 2021

(86) PCT No.: PCT/CN2021/092406

§ 371 (c)(1),
(2) Date: Nov. 8, 2022

(87) PCT Pub. No.: WO2021/227989

PCT Pub. Date: Nov. 18, 2021

(65) Prior Publication Data

US 2023/0174608 A1 Jun. 8, 2023

(30) Foreign Application Priority Data

May 9, 2020 (CN) ......................... 202010388208.0

(51) Int. Cl.

*C07K 14/605* (2006.01)
*A61K 38/26* (2006.01)
*A61P 3/00* (2006.01)
*A61P 3/04* (2006.01)
*A61P 3/10* (2006.01)
*A61K 38/00* (2006.01)

(52) U.S. Cl.

CPC .............. *C07K 14/605* (2013.01); *A61P 3/04* (2018.01); *A61P 3/10* (2018.01); *A61K 38/00* (2013.01)

(58) Field of Classification Search

CPC .. C07K 14/605; A61P 3/04; A61P 3/10; A61P 3/00; A61P 3/06; A61K 38/00; A61K 38/26

See application file for complete search history.

(56) References Cited

U.S. PATENT DOCUMENTS

2013/0157953 A1* 6/2013 Petersen .................. A61P 9/10 514/11.7
2024/0252592 A1* 8/2024 Han .......................... A61P 3/10

FOREIGN PATENT DOCUMENTS

| | | | |
|---|---|---|---|
| CN | 102892425 | A | 1/2011 |
| CN | 108341880 | A | 7/2018 |
| CN | 103732618 | A | 10/2018 |
| JP | 2013517307 | | 5/2013 |
| JP | 2017503474 | A | 2/2017 |
| KR | 10-2012-0137271 | | 12/2012 |
| WO | 2011088837 | A1 | 7/2011 |
| WO | 2012169798 | A2 | 12/2012 |
| WO | 2012169798 | A3 | 12/2012 |

OTHER PUBLICATIONS

International Search Report [ISA/CN] PCT/CN2021/092406, dated Jun. 25, 2021.
Notification of Reason for Refusal (JP 2022-567566) dated Oct. 18, 2023.
Extended European Search Report, EP 201803512.9, dated May 14, 2024.
KR 1020227043172, Notice of Preliminary Rejection, unknown date.
China Search Report, CN 2021105016148, dated Apr. 21, 2026.

* cited by examiner

*Primary Examiner* — Julie Ha
*Assistant Examiner* — Kristina M Hellman
(74) *Attorney, Agent, or Firm* — Edwin S. Flores; Daniel J. Chalker; Chalker Flores, LLP

(57) ABSTRACT

The present invention provides a polypeptide derivative, or a modified derivative or salt thereof, and use of the polypeptide derivative, or the modified derivative or salt thereof. The polypeptide derivative, or the modified derivative or salt thereof comprises a polypeptide having the sequence of the following general formula I: general formula I: $HX^{2}QGTFTSDX^{10}SKYLX^{15}EX^{17}X^{18}AX^{20}X^{21}FX^{23}AWLEX^{28}X^{29}X^{30}$, wherein the definitions of $X^2$, $X^{10}$, $X^{15}$, $X^{17}$, $X^{18}$, $X^{20}$, $X^{21}$, $X^{23}$, $X^{28}$, $X^{29}$, and $X^{30}$ are consistent with those in the claims and description. The polypeptide derivatives of the present invention are dual agonists for GC/GLP-1 receptor, have a synergic effect on energy metabolism, can effectively reduce weight and improve a body fat level while reducing blood glucose, and have a potential application value in the field of treatment of metabolic diseases such as diabetes and obesity.

12 Claims, 2 Drawing Sheets

Specification includes a Sequence Listing.

SEQUENCE LISTING

<160> NUMBER OF SEQ ID NOS: 32

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg
20 25 30

<210> SEQ ID NO 2
<211> LENGTH: 29
<212> TYPE: PRT
<213> ORGANISM: Homo sapiens

<400> SEQUENCE: 2

His Ser Gln Gly Thr Phe Thr Ser Asp Tyr Ser Lys Tyr Leu Asp Ser

-continued

```
1               5                   10                  15

Arg Arg Ala Gln Asp Phe Val Gln Trp Leu Met Asn Thr
            20                  25


<210> SEQ ID NO 3
<211> LENGTH: 37
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35


<210> SEQ ID NO 4
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: BINDING
<222> LOCATION: (20)..(20)
<223> OTHER INFORMATION: The side chain of Lys is modified

<400> SEQUENCE: 4

His Ser Gln Gly Thr Phe Thr Ser Asp Tyr Ser Lys Tyr Leu Asp Glu
1               5                   10                  15

Arg Ala Ala Lys Glu Phe Ile Ala Trp Leu Glu Ala Gly Gly
            20                  25                  30


<210> SEQ ID NO 5
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Serine is D-Ser
<220> FEATURE:
<221> NAME/KEY: BINDING
<222> LOCATION: (20)..(20)
<223> OTHER INFORMATION: The side chain of Lys is modified

<400> SEQUENCE: 5

His Ser Gln Gly Thr Phe Thr Ser Asp Tyr Ser Lys Tyr Leu Glu Glu
1               5                   10                  15

Lys Ala Ala Lys Glu Phe Ile Ala Trp Leu Glu Ala Gly Gly
            20                  25                  30


<210> SEQ ID NO 6
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Serine is D-Ser
<220> FEATURE:
<221> NAME/KEY: BINDING
```

<222> LOCATION: (20)..(20)
<223> OTHER INFORMATION: The side chain of Lys is modified

<400> SEQUENCE: 6

```
His Ser Gln Gly Thr Phe Thr Ser Asp Tyr Ser Lys Tyr Leu Glu Glu
1               5                   10                  15

Arg Ala Ala Lys Glu Phe Ile Ala Trp Leu Glu Ala Gly Gly
            20                  25                  30
```

<210> SEQ ID NO 7
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 7

```
His Xaa Gln Gly Thr Phe Thr Ser Asp Tyr Ser Lys Tyr Leu Asp Glu
1               5                   10                  15

Arg Ala Ala Lys Glu Phe Ile Ala Trp Leu Glu Ala Gly Gly
            20                  25                  30
```

<210> SEQ ID NO 8
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 8

```
His Xaa Gln Gly Thr Phe Thr Ser Asp Tyr Ser Lys Tyr Leu Glu Glu
1               5                   10                  15

Arg Ala Ala Lys Glu Phe Ile Ala Trp Leu Glu Ala Gly Gly
            20                  25                  30
```

<210> SEQ ID NO 9
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 9

```
His Xaa Gln Gly Thr Phe Thr Ser Asp Tyr Ser Lys Tyr Leu Asp Glu
1               5                   10                  15
```

```
Arg Ala Ala Lys Glu Phe Val Ala Trp Leu Glu Ala Gly Gly
            20                  25                  30


<210> SEQ ID NO 10
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: BINDING
<222> LOCATION: (20)..(20)
<223> OTHER INFORMATION: The side chain of Lys is modified

<400> SEQUENCE: 10

His Ser Gln Gly Thr Phe Thr Ser Asp Tyr Ser Lys Tyr Leu Asp Glu
1               5                   10                  15

Arg Ala Ala Lys Glu Phe Ile Ala Trp Leu Glu Ser Gly Gly
            20                  25                  30


<210> SEQ ID NO 11
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Serine is D-Ser
<220> FEATURE:
<221> NAME/KEY: BINDING
<222> LOCATION: (20)..(20)
<223> OTHER INFORMATION: The side chain of Lys is modified

<400> SEQUENCE: 11

His Ser Gln Gly Thr Phe Thr Ser Asp Tyr Ser Lys Tyr Leu Glu Glu
1               5                   10                  15

Arg Ala Ala Lys Glu Phe Val Ala Trp Leu Glu Ser Gly Gly
            20                  25                  30


<210> SEQ ID NO 12
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 12

His Xaa Gln Gly Thr Phe Thr Ser Asp Tyr Ser Lys Tyr Leu Asp Glu
1               5                   10                  15

Arg Ala Ala Lys Glu Phe Ile Ala Trp Leu Glu Ser Gly Gly
            20                  25                  30


<210> SEQ ID NO 13
<211> LENGTH: 30
<212> TYPE: PRT
<213> ORGANISM: Artificial Sequence
<220> FEATURE:
<223> OTHER INFORMATION: Glucagon-derived peptide
```

<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 13

```
His Xaa Gln Gly Thr Phe Thr Ser Asp Tyr Ser Lys Tyr Leu Glu Glu
1               5                   10                  15

Arg Ala Ala Lys Glu Phe Ile Ala Trp Leu Glu Ser Gly Gly
            20                  25                  30
```

<210> SEQ ID NO 14
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 14

```
His Xaa Gln Gly Thr Phe Thr Ser Asp Tyr Ser Lys Tyr Leu Glu Glu
1               5                   10                  15

Lys Ala Ala Lys Glu Phe Val Ala Trp Leu Glu Ser Gly Gly
            20                  25                  30
```

<210> SEQ ID NO 15
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 15

```
His Xaa Gln Gly Thr Phe Thr Ser Asp Tyr Ser Lys Tyr Leu Asp Glu
1               5                   10                  15

Lys Ala Ala Lys Glu Phe Ile Ala Trp Leu Glu Ser Gly Gly
            20                  25                  30
```

<210> SEQ ID NO 16
<211> LENGTH: 29
<212> TYPE: PRT
<213> ORGANISM: Artificial Sequence
<220> FEATURE:
<223> OTHER INFORMATION: Glucagon-derived peptide
<220> FEATURE:
<221> NAME/KEY: BINDING
<222> LOCATION: (20)..(20)
<223> OTHER INFORMATION: The side chain of Lys is modified

<400> SEQUENCE: 16

```
His Ser Gln Gly Thr Phe Thr Ser Asp Tyr Ser Lys Tyr Leu Asp Glu
1               5                   10                  15

Arg Ala Ala Lys Glu Phe Ile Ala Trp Leu Glu Gly Gly
            20                  25


<210> SEQ ID NO 17
<211> LENGTH: 29
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Serine is D-Ser
<220> FEATURE:
<221> NAME/KEY: BINDING
<222> LOCATION: (20)..(20)
<223> OTHER INFORMATION: The side chain of Lys is modified

<400> SEQUENCE: 17

His Ser Gln Gly Thr Phe Thr Ser Asp Tyr Ser Lys Tyr Leu Glu Glu
1               5                   10                  15

Arg Ala Ala Lys Glu Phe Val Ala Trp Leu Glu Gly Gly
            20                  25


<210> SEQ ID NO 18
<211> LENGTH: 29
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 18

His Xaa Gln Gly Thr Phe Thr Ser Asp Tyr Ser Lys Tyr Leu Asp Glu
1               5                   10                  15

Arg Ala Ala Lys Glu Phe Ile Ala Trp Leu Glu Gly Gly
            20                  25


<210> SEQ ID NO 19
<211> LENGTH: 29
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 19

His Xaa Gln Gly Thr Phe Thr Ser Asp Tyr Ser Lys Tyr Leu Glu Glu
1               5                   10                  15

Arg Ala Ala Lys Glu Phe Ile Ala Trp Leu Glu Gly Gly
            20                  25
```

```
<210> SEQ ID NO 20
<211> LENGTH: 29
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 20

His Xaa Gln Gly Thr Phe Thr Ser Asp Tyr Ser Lys Tyr Leu Glu Glu
1               5                   10                  15

Lys Ala Ala Lys Glu Phe Val Ala Trp Leu Glu Gly Gly
            20                  25


<210> SEQ ID NO 21
<211> LENGTH: 29
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 21

His Xaa Gln Gly Thr Phe Thr Ser Asp Tyr Ser Lys Tyr Leu Asp Glu
1               5                   10                  15

Lys Ala Ala Lys Glu Phe Ile Ala Trp Leu Glu Gly Gly
            20                  25


<210> SEQ ID NO 22
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: BINDING
<222> LOCATION: (20)..(20)
<223> OTHER INFORMATION: The side chain of Lys is modified

<400> SEQUENCE: 22

His Ser Gln Gly Thr Phe Thr Ser Asp Tyr Ser Lys Tyr Leu Asp Glu
1               5                   10                  15

Arg Ala Ala Lys Glu Phe Ile Ala Trp Leu Glu Gly Glu Gly
            20                  25                  30


<210> SEQ ID NO 23
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Serine is D-Ser
<220> FEATURE:
```

<221> NAME/KEY: BINDING
<222> LOCATION: (20)..(20)
<223> OTHER INFORMATION: The side chain of Lys is modified

<400> SEQUENCE: 23

His Ser Gln Gly Thr Phe Thr Ser Asp Tyr Ser Lys Tyr Leu Glu Glu
1 5 10 15

Lys Ala Ala Lys Glu Phe Val Ala Trp Leu Glu Gly Glu Gly
20 25 30

<210> SEQ ID NO 24
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 24

His Xaa Gln Gly Thr Phe Thr Ser Asp Tyr Ser Lys Tyr Leu Asp Glu
1 5 10 15

Arg Ala Ala Lys Glu Phe Ile Ala Trp Leu Glu Gly Glu Gly
20 25 30

<210> SEQ ID NO 25
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 25

His Xaa Gln Gly Thr Phe Thr Ser Asp Tyr Ser Lys Tyr Leu Glu Glu
1 5 10 15

Arg Ala Ala Lys Glu Phe Ile Ala Trp Leu Glu Gly Glu Gly
20 25 30

<210> SEQ ID NO 26
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 26

His Xaa Gln Gly Thr Phe Thr Ser Asp Tyr Ser Lys Tyr Leu Glu Glu

```
1               5                   10                  15

Lys Ala Ala Lys Glu Phe Val Ala Trp Leu Glu Gly Glu Gly
            20                  25                  30


<210> SEQ ID NO 27
<211> LENGTH: 30
<212> TYPE: PRT
<213> ORGANISM: Artificial Sequence
<220> FEATURE:
<223> OTHER INFORMATION: Glucagon-derived peptide
<220> FEATURE:
<221> NAME/KEY: MUTAGEN
<222> LOCATION: (2)..(2)
<223> OTHER INFORMATION: Xaa is alpha-aminoisobutyric acid
<220> FEATURE:
<221> NAME/KEY: BINDING
<222> LOCATION: (20)..(20)
<223> OTHER INFORMATION: The side chain of Lys is modified

<400> SEQUENCE: 27

His Xaa Gln Gly Thr Phe Thr Ser Asp Tyr Ser Lys Tyr Leu Asp Glu
1               5                   10                  15

Lys Ala Ala Lys Glu Phe Ile Ala Trp Leu Glu Gly Glu Gly
            20                  25                  30


<210> SEQ ID NO 28
<211> LENGTH: 31
<212> TYPE: PRT
<213> ORGANISM: Homo sapiens

<400> SEQUENCE: 28

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 29
<211> LENGTH: 10
<212> TYPE: PRT
<213> ORGANISM: Artificial Sequence
<220> FEATURE:
<223> OTHER INFORMATION: C terminus 10 peptides of Exendin-4

<400> SEQUENCE: 29

Gly Pro Ser Ser Gly Ala Pro Pro Pro Ser
1               5                   10


<210> SEQ ID NO 30
<211> LENGTH: 8
<212> TYPE: PRT
<213> ORGANISM: Homo sapiens

<400> SEQUENCE: 30

Lys Arg Asn Arg Asn Asn Ile Ala
1               5


<210> SEQ ID NO 31
<211> LENGTH: 6
<212> TYPE: PRT
<213> ORGANISM: Artificial Sequence
<220> FEATURE:
<223> OTHER INFORMATION: Peptide fragment

<400> SEQUENCE: 31

Gly Gly Pro Ser Ser Gly
1               5
```

<210> SEQ ID NO 32
<211> LENGTH: 30
<212> TYPE: PRT
<213> ORGANISM: Artificial Sequence
<220> FEATURE:
<223> OTHER INFORMATION: General Formula I
<220> FEATURE:
<221> NAME/KEY: MUTAGEN
<222> LOCATION: (2)..(2)
<223> OTHER INFORMATION: Xaa is Ser, D-Ser or Aib
<220> FEATURE:
<221> NAME/KEY: MUTAGEN
<222> LOCATION: (10)..(10)
<223> OTHER INFORMATION: Xaa is Tyr
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (17)..(17)
<223> OTHER INFORMATION: Xaa is Arg, Gln or Lys
<220> FEATURE:
<221> NAME/KEY: MUTAGEN
<222> LOCATION: (18)..(18)
<223> OTHER INFORMATION: Xaa is Ala
<220> FEATURE:
<221> NAME/KEY: BINDING
<222> LOCATION: (20)..(20)
<223> OTHER INFORMATION: The side chain of Lys is modified
<220> FEATURE:
<221> NAME/KEY: MUTAGEN
<222> LOCATION: (21)..(21)
<223> OTHER INFORMATION: Xaa is Asp or Glu
<220> FEATURE:
<221> NAME/KEY: MUTAGEN
<222> LOCATION: (23)..(23)
<223> OTHER INFORMATION: Xaa is Val or Ile
<220> FEATURE:
<221> NAME/KEY: MUTAGEN
<222> LOCATION: (28)..(28)
<223> OTHER INFORMATION: Xaa is Ala, Gly or Ser
<220> FEATURE:
<221> NAME/KEY: MUTAGEN
<222> LOCATION: (29)..(29)
<223> OTHER INFORMATION: Xaa is Gly or Glu
<220> FEATURE:
<221> NAME/KEY: MUTAGEN
<222> LOCATION: (30)..(30)
<223> OTHER INFORMATION: Xaa is Gly or absent

<400> SEQUENCE: 32

```
His Xaa Gln Gly Thr Phe Thr Ser Asp Xaa Ser Lys Tyr Leu Xaa Glu
1               5                   10                  15

Xaa Xaa Ala Xaa Xaa Phe Xaa Ala Trp Leu Glu Xaa Xaa Xaa
            20                  25                  30
```

POLYPEPTIDE DERIVATIVE HAVING DUAL RECEPTOR AGONISTIC ACTION AND USE THEREOF

CROSS-REFERENCE TO RELATED APPLICATIONS

This application claim priority to and is the National Stage of International Application No. PCT/CN2021/092406, filed on May 8, 2021 claiming the priority of CN 202010388208.0, filed on May 9, 2020, the content of each of which is incorporated by reference herein.

TECHNICAL FIELD

The present invention belongs to the technical field of medical biology, and particularly relates to glucagon-derived peptides having glucagon/glucagon-like peptide 1 dual receptor agonistic action and use thereof.

BACKGROUND ART

Obesity is a risk factor for a variety of diseases and has been a global public health issue. Especially, incidence rates and progression of common diseases such as metabolic syndrome including type-2 diabetes mellitus (T2DM), cardiovascular diseases, and non-alcoholic fatty liver disease are closely associated with obesity. Many clinical studies of large samples have found that incidence rates of cardiometabolic multiple diseases are 2-time, 5-time, and 15-time higher in overweight, obese, and severely obese populations with BMI of 25.0-29.9 kg/m$^2$, 30.0-34.9 kg/m$^2$, and >35.0 kg/m$^2$, respectively, compared with normal weight populations (Lancet 2, e277-e285, 2017). Studies have shown that 80-90% of patients with T2DM are overweight or obese, and moderate weight loss (4-5 kg) is beneficial for prevention and control of conditions, including reduction of the morbidity rate, and control of blood glucose and the disability (mortality) rate (Curr. Med. Res. Opin. 2011, 27 (7), 1431-1438).

Diet control and exercise are the most desirable means of weight loss, but are generally ineffective. Pharmacological interventions for obesity have limited efficacy or carry multiple risks, including severe impacts on the cardiovascular system and side effects such as psychiatric symptoms due to the action on the central nervous system. So far, few drugs alone have been able to achieve more than 5-10% weight loss. Among drugs for treating T2DM, only SGLT2 inhibitors and GLP-1 receptor agonists have good weight control effects. Bariatric surgery has significant efficacy but large risk, and long-term effects remain uncertain. Therefore, there is still a huge clinical demand for drugs for controlling weight, and drugs that combine a therapeutic effect on primary symptoms with the ability to control weight safely and effectively are an ideal choice.

Blood glucose and energy regulatory signaling systems of the body are maintained in a delicate balance by a variety of factors, including different polypeptide hormones. Proglucagon is a precursor polypeptide having 158 amino acids, which is processed in different tissues to yield a variety of pro-glucagon-derived peptides such as glucagon (GC), glucagon-like peptides 1 and 2 (GLP-1 and 2), and oxyntomodulin, and these hormones are involved in the regulation of various physiological functions such as glucose homeostasis, insulin secretion, gastric emptying, intestinal growth, and food intake. Therefore, treatment based on pro-glucagon-derived intestinal hormones has become a research direction of great concern in the field of metabolic diseases.

GC is a derived peptide containing 29 amino acids corresponding to the 33rd amino acid to the 61st amino acids in pro-glucagon, which is processed and produced by pancreatic a cells, and acts on the liver to raise a blood glucose level to the normal range through glycolysis and gluconeogenesis when the body is in stress states such as hunger and cold. Results of animal and human experiments have shown that in addition to the action of raising blood glucose, GC also has actions such as thermogenesis, increasing satiety, lipolysis, fat oxidation, and ketogenesis, and long-term administration can improve energy metabolism, including weight loss. However, these beneficial effects on energy metabolism have not been applied due to its inherent glucose-raising effects.

GLP-1 is a derived peptide containing 37 amino acid residues corresponding to the 72nd amino acid to the 108th amino acid in pro-glucagon, which is secreted by intestinal L cells in response to food intake, acts on pancreatic (3-cells to promote insulin secretion, and antagonizes GC receptor to inhibit the rise of blood glucose. GLP-1 receptor agonists are developed as therapeutic agents for hyperglycemia in patients with diabetes, which reduces blood glucose along with protecting and proliferating islet cells, and can effectively decrease body weight through retarding gastric emptying and inhibiting food intake. 7 GLP-1 receptor agonists have been marketed, including short-acting exenatide, liraglutide, and lixisenatide (administered once or twice a day), and long-acting albiglutide, dulaglutide, Byuderon, and semaglutide (administered once a week). Although GLP-1 receptor agonist drugs have safe and unique effects of lowering blood glucose, their use for weight loss generally requires a high dose. Furthermore, these drugs at high doses are prone to gastrointestinal side effects, poor tolerance and a narrow therapeutic window. Therefore, there is still a need for more tolerant therapeutic agents capable of effectively controlling blood glucose and reducing weight.

Oxyntomodulin (OXM) is a hormone produced in the intestinal tract during post-translational modification of proglucagon, which is secreted from ileal L-cells in response to food intake along with hormones such as GLP-1. Acute effects of OXM include inhibition of gastric emptying, gastric and pancreatic exo-secretion, and food intake, resting energy expenditure, etc., resulting in weight loss. OXM-specific receptors have not yet been identified, but studies have found that OXM is a dual agonist for endogenous GCGR/GLP-1R, and its active effects on the two receptors are weaker than those of natural ligands of both receptors. In animal and human experiments, it has been found that peripheral administration of OXM can reduce food intake and cause weight loss, and increase metabolic rate, especially activity-related energy expenditure in obese subjects. Especially, in clinical trials, the occurrence rates of common gastrointestinal side effects such as nausea and vomiting were low when OXM was given peripherally at a high dose to reduce weight. Therefore, treatment based on OXM or a dual agonist for GLP-1/GCGR shows potential application value for obesity and obese diabetes. However, so far, no relevant drugs have been marketed.

SUMMARY OF THE INVENTION

One object of the present invention is to provide a polypeptide derivative of glucagon, which is a variant designed from natural GC sequence, and has synergistic effect on energy metabolism through the dual agonistic action on GC/GLP-1 receptors, which can effectively lower blood glucose, reduce body weight, and improve body fat level, and can be used for treating diseases such as diabetes, obesity, metabolic syndrome, and non-alcoholic fatty liver disease.

Another object of the present invention is to provide a pharmaceutical composition comprising the polypeptide derivative of glucagon of the present invention.

Still another object of the present invention is to provide use of the polypeptide derivative of glucagon of the present invention.

The objects of the present invention are achieved by the following technical solutions.

In one aspect, the present invention provides a polypeptide derivative, or a modified derivative or salt thereof, comprising a polypeptide having a sequence of the following general formula I:

General Formula I (SEQ ID NO. 32)

$HX^{2}QGTFTSDX^{10}SKYLX^{15}EX^{17}X^{18}AX^{20}X^{21}FX^{23}AWLEX^{28}X^{29}X^{30}$ wherein, $X^2$ is Ser, D-Ser or Aib;
$X^{10}$ is Tyr;
$X^{15}$ is Asp or Glu;
$X^{27}$ is Arg, Gln or Lys;
$X^{18}$ is Ala;
$X^{20}$ is Lys with the side chain being modified;
$X^{21}$ is Asp or Glu;
$X^{23}$ is Val or Ile;
$X^{28}$ is Ala, Gly or Ser;
$X^{29}$ is Gly or Glu;
$X^{30}$ is Gly or absent; and
the C-terminal carboxyl group is free or amidated.

In some preferred embodiments, in the sequence of the general formula I,
$X^{17}$ is Arg or Lys;
$X^{28}$ is Ala or Ser;
$X^{29}$ is Gly;
$X^{30}$ is Gly; and
the C-terminal carboxyl group is amidated.

In a preferred embodiment, in the sequence of the general formula I, $X^2$ is Aib.

In a preferred embodiment, the sequence of the general formula I is selected from

SEQ ID NO. 4:
HSQGTFTSDYSKYLDERAAK*EFIAWLEAGG;

SEQ ID NO. 5:
HdSQGTFTSDYSKYLEEKAAK*EFIAWLEAGG;

SEQ ID NO. 6:
HdSQGTFTSDYSKYLEERAAK*EFIAWLEAGG;

SEQ ID NO. 7:
HAibQGTFTSDYSKYLDERAAK*EFIAWLEAGG;

SEQ ID NO. 8:
HAibQGTFTSDYSKYLEERAAK*EFIAWLEAGG;

SEQ ID NO. 9:
HAibQGTFTSDYSKYLDERAAK*EFVAWLEAGG;

SEQ ID NO. 10:
HSQGTFTSDYSKYLDERAAK*EFIAWLESGG;

-continued

SEQ ID NO. 11:
HdSQGTFTSDYSKYLEERAAK*EFVAWLESGG;

SEQ ID NO. 12:
HAibQGTFTSDYSKYLDERAAK*EFIAWLESGG;

SEQ ID NO. 13:
HAibQGTFTSDYSKYLEERAAK*EFIAWLESGG;

SEQ ID NO. 14:
HAibQGTFTSDYSKYLEEKAAK*EFVAWLESGG;
and

SEQ ID NO. 15:
HAibQGTFTSDYSKYLDEKAAK*EFIAWLESGG, wherein in SEQ ID NO. 4 to SEQ ID NO. 15, K* is Lys with the side chain ε-amino group being modified, and the C-terminal carboxyl group is amidated.

In some preferred embodiments, in the sequence of the general formula I,
$X^{17}$ is Arg or Lys;
$X^{28}$ is Gly;
$X^{29}$ is Gly;
$X^{30}$ is absent; and
the C-terminal carboxyl group is amidated.

In a preferred embodiment, the sequence of the general formula I is selected from:

SEQ ID NO. 16:
HSQGTFTSDYSKYLDERAAK*EFIAWLEGG;

SEQ ID NO. 17:
HdSQGTFTSDYSKYLEERAAK*EFVAWLEGG;

SEQ ID NO. 18:
HAibQGTFTSDYSKYLDERAAK*EFIAWLEGG;

SEQ ID NO. 19:
HAibQGTFTSDYSKYLEERAAK*EFIAWLEGG;

SEQ ID NO. 20:
HAibQGTFTSDYSKYLEEKAAK*EFVAWLEGG:
and

SEQ ID NO. 21:
HAibQGTFTSDYSKYLDEKAAK*EFIAWLEGG, wherein in SEQ ID NO. 16 to SEQ ID NO. 21, K* is Lys with the side chain ε-amino group being modified, and the C-terminal carboxyl group is amidated.

In some preferred embodiments, in the sequence of the general formula I,
$X^{17}$ is Arg or Lys;
$X^{28}$ is Gly;
$X^{29}$ is Glu;
$X^{30}$ is Gly; and
the C-terminal carboxyl group is amidated.

In a preferred embodiment, the sequence of the general formula I is selected from:

SEQ ID NO. 22:
HSQGTFTSDYSKYLDERAAK*EFIAWLEGEG;

SEQ ID NO. 23:
HdSQGTFTSDYSKYLEEKAAK*EFVAWLEGEG;

SEQ ID NO. 24:
HAibQGTFTSDYSKYLDERAAK*EFIAWLEGEG;

SEQ ID NO. 25:
HAibQGTFTSDYSKYLEERAAK*EFIAWLEGEG;

-continued

```
SEQ ID NO. 26:
HAibQGTFTSDYSKYLEEKAAK*EFVAWLEGEG;
and

SEQ ID NO. 27:
HAibQGTFTSDYSKYLDEKAAK*EFIAWLEGEG,
```

wherein in SEQ ID NO. 22 to SEQ ID NO. 27, K* is Lys with the side chain ε-amino group being modified, and the C-terminal carboxyl group is amidated.

In some preferred embodiments of the present invention, the Lys with the side chain being modified means that the side chain ε-amino group of the Lys is modified by coupling to a fatty acyl group through a hydrophilic linker fragment.

Preferably, the hydrophilic linker fragment used for modifying the side chain ε-amino group of Lys is selected from fragments consisting of one or more of Glu, γGlu, Gly, and Ado (8-amino-3,6-dioxaoctanoic acid). Preferably, the hydrophilic linker fragment is -γGlu-, -γGlu-γGlu-, -Glu-γGlu-, -γGlu-Gly-Gly-, -γGlu-Gly-γGlu-, -γGlu-Ado-Ado-, -Ado-Ado-γGlu- or -γGlu-Ado-Ado-γGlu-.

In a preferred embodiment of the present invention, the fatty acyl group is a $C_{14}$-20 fatty acyl group, including $C_{14}$-20 monofatty acyl group and fatty diacid monoacyl group, more preferably, a $C_{16}$-18 fatty acyl group, and the most preferably, a $C_{16}$ monofatty acyl group (a palmitoyl group).

In another aspect, the present invention provides a pharmaceutical composition, comprising the polypeptide derivative, or the modified derivative or salt thereof of the present invention and optionally one or more pharmaceutically acceptable adjuvants.

Preferably, the pharmaceutically acceptable adjuvants include a carrier, a diluent, a water-soluble filler, a pH regulator, a stabilizer, water for injection, an osmotic pressure regulator, etc.

Preferably, the water-soluble filler includes, but is not limited to, mannitol, low-molecular-weight dextran, sorbitol, polyethylene glycol, glucose, lactose, and galactose; the pH regulator includes, but is not limited to, organic and inorganic acids such as citric acid, phosphoric acid, lactic acid, tartaric acid, and hydrochloric acid, and the like, and physiologically acceptable inorganic bases or salts such as potassium hydroxide, sodium hydroxide, ammonium hydroxide, sodium carbonate, potassium carbonate, ammonium carbonate, potassium bicarbonate, sodium bicarbonate, and ammonium bicarbonate, and the like; the stabilizer includes, but is not limited to, EDTA-2Na, sodium thiosulfate, sodium pyrosulfite, sodium sulfite, dipotassium hydrogen phosphate, sodium bicarbonate, sodium carbonate, arginine, lysine, glutamic acid, aspartic acid, polyethylene glycol, polyvinyl alcohol, polyvinylpyrrolidone, carboxyl/hydroxyl cellulose and derivatives thereof such as HPC, HPC-SL, HPC-L, and HPMC, cyclodextrin, sodium dodecyl sulfate, and tris(hydroxymethyl)aminomethane; and the osmotic pressure regulator includes, but is not limited to, sodium chloride and potassium chloride.

Preferably, the pharmaceutical composition of the present invention can be injected intravenously, intramuscularly or subcutaneously, or administered orally, rectally or nasally. A therapeutic dose range is determined by a subject to be treated, a mode of administration, indications, and other factors.

In still another aspect, the present invention provides use of the polypeptide derivative, or the modified derivative or salt thereof of the present invention in the preparation of a medicament for treating a metabolic disease, preferably, the metabolic disease is diabetes, obesity, fatty liver disease, hyperlipidemia and/or metabolic syndrome, and more preferably, the fatty liver disease is non-alcoholic fatty liver disease.

In another aspect, the present invention provides a method for treating a metabolic disease, comprising administering a therapeutically effective amount of the polypeptide derivative, the modified derivative or salt thereof of the present invention, or the pharmaceutical composition of the present invention to a patient in need thereof, preferably, the metabolic disease is diabetes, obesity, fatty liver disease, hyperlipidemia and/or metabolic syndrome, and more preferably, the fatty liver disease is non-alcoholic fatty liver disease.

Structure of a glucagon-derived peptide: endogenous GLP-1 is a derived peptide containing 30-31 amino acid residues (7-36/37) corresponding to the 72nd amino acid to the 108th amino acid in pro-glucagon, and its amino acid sequence is HAEGTFTSDVSSYLEGQAAKEFIAWLVKGR (7-36) (SEQ ID NO. 1) or HAEGTFTSDVSSYLEGQAAKEFIAWLVKGRG (7-37) (SEQ ID NO. 28) in which the C-terminal carboxyl group is free or amidated. Endogenous GC is a derived peptide containing 29 amino acids corresponding to the 33rd amino acid to the 61st amino acid in pro-glucagon, and its amino acid sequence is HSQGTFTSDYSKYLDSRRAQDFVQWLMNT (SEQ ID NO. 2) in which the C-terminal carboxyl group is free. Natural GLP-1 and GC have 47% of homology in the amino acid sequences (Andreas Evers et al. J. Med. Chem. 2017, 60, 4293-4303), the N-terminal sequences of the two are highly conservative, GLP-1 is highly selective for its receptor, and GC is also a weak agonist for the GLP-1 receptor.

Oxyntomodulin (OXM) is an endogenous dual agonist for GC/GLP-1R, and its amino acid sequence is HSQGTFTSDYSKYLDSRRAQDFVQWLMNTKRNRNNIA (SEQ ID NO. 3), which comprises an original GC sequence (1-29) and an inserted peptide-1 (IP-1, 30-37) corresponding to the sequence of 82nd amino acid to the 89th amino acid in pro-glucagon. In the prior art documents using OXM as a leader sequence, such as CN200980132562.9, CN201080027026.5, and CN201680062196.4, the C terminus of a variant of the original GC sequence (1-29) is extended with a sequence of C terminus 10 peptides (GPSSGAPPPS (SEQ ID NO. 29, Cex for short) of Exendin-4. In CN201680036771.3, a design scheme for replacing the C-terminal inserted peptide fragment (KRNRNNIA (SEQ ID NO. 30)) of the OXM sequence with a peptide fragment GGPSSG (SEQ ID NO. 31) is used. All the prior art documents adopted the design idea of mutating several sites on the basis of retaining the full-length GC sequence (1-29) and then extending the sequence with different peptide fragments.

When a dual agonist is designed based on the GC sequence, in order to obtain an expected balanced potency ratio, in most of the prior art documents, a fragment from the 16th site to the 23rd site in the GC sequence is similarly replaced with a corresponding GLP-1 sequence, or individual sites, such as the 16th site, the 17th site, the 18th site, the 20th site, and the 23rd site, are mutated. Changes to the C terminus of the GC sequence are extremely sensitive to the recognition of GC/GLP-1 receptors, especially to the activity of the GC receptor. Therefore, in most of the technical solutions in the prior art documents, an original sequence of a fragment from the 27th site to the 29th site at the C terminus is retained, and only in a few technical solutions of the prior art documents, conservative mutations are performed, for example, sensitive amino acid 27Met is replaced with Leu, and 28Asn is replaced with Glu or Ala. Long-chain fatty acyl modification on a polypeptide sequence is generally intended to prolong in vivo half-life of the polypeptide, but when applied to the design of a dual agonist for GC/GLP-1 receptors, modification at an appropriate site can adjust the balance between the selectivity to receptors and the activity. In most of the prior art documents, the ε-side chain of a mutated $^{10}$Lys residue is modified with a palmitoyl group to obtain a strong agonist (EC50 μM) with balanced potency. However, the inventors of the present invention have found that these strong agonists result in impaired glucose tolerance when administered to model animals for a long time in an in vivo efficacy evaluation, and cannot achieve an expected metabolism regulation purpose.

By a comprehensive survey of the prior art documents, it can be found that due to the structural complexity of a long-chain polypeptide and the particularity of the binding of the long-chain polypeptide to its receptor, the acquisition of a dual agonist with the appropriate active strength and a balanced potency ratio requires a rational combination of different technical measures. Changes to the structure of the polypeptide, such as mutation of amino acid residues at different sites, modification of sites, and changes in groups, will cause unpredictable changes in the balance of activity and potency ratio.

In the technical solutions provided by the present invention, a design idea for the main chain of a polypeptide is that individual sites in a fragment from the 1st site to the 26th site in the GC sequence are properly mutated, then the C terminus is appropriately extended, and the side chain is modified, for example, the 20th site is modified with a fatty acyl group, such that a dual agonist for GC/GLP-1 receptors that has a balanced activity and potency ratio and good solubility and stability is obtained.

In some specific embodiments of the present invention, the 16th site to the 20th site in the GC sequence (1-26) are properly replaced, for example, 16Ser is replaced with Glu, 18Arg is replaced with Ala or Lys, etc., which are mutations conducive to improvement of the GLP-1 receptor selectivity. Unlike the conservative replacement scheme of the C terminus of the GC sequence in most of the disclosed technical solutions, a preferred technical solution of the present invention is to replace 27Met with Glu, and replace the 28th site and the 29th site with electrically neutral amino acids such as Gly and Ala. It is generally acknowledged that the free C-terminal carboxyl group of the GC sequence is beneficial to retention of the activity. In an embodiment of the present invention, 27Met is replaced with Glu to retain the electronegativity of the C terminus so as to reduce an impact on the activity, and the C-terminus is further amidated to improve the stability of the peptide sequence.

In general, it is beneficial to retain homology by making as few changes as possible to a natural sequence, but the design based on the endogenous pro-glucagon sequence has many problems in druggability: the N-terminal dipeptide is easily recognized by a dipeptidyl peptidase in vivo and hydrolytically inactivated, resulting in a short plasma half-life (≤12 min); the sequence has unstable physical properties, that is, the sequence has an isoelectric point (pI) of 7.6, is neutral and hydrophobic, has poor solubility, and easily aggregates and precipitates in a solution; and the sequence contains amino acids that are prone to oxidation or racemization, such as Met, Asp, and Asn, resulting in unstable chemical properties.

In a preferred embodiment of the present invention, 2Ser in the polypeptide sequence is generally replaced with Aib or D-Ser to improve the stability of metabolism, thereby ensuring continuous exertion of the polypeptide activity. Meanwhile, in a preferred embodiment of the present invention, sensitive amino acids in the GC sequence are further replaced, for example, 15Asp and 21Asp are replaced with Glu.

After the above adjustments, the number of negative charges at the sequence C terminus of the polypeptide sequence is increased, and the pI value is reduced, which is beneficial to improvement of the solubility of the peptide under physiological conditions and the chemical stability.

The structure of a fatty acyl group and a linker as well as modification sites together affect the activity of a compound. In an embodiment of the present invention, on the side chain of Lys at the 20th site in the peptide sequence, a fatty acyl group is modified with a hydrophilic linker arm. In certain embodiments of the present invention, the hydrophilic linker arm is -γ-Glu- or -γ-Glu-γ-Glu-, and in some other embodiments, the hydrophilic linker arm is -Ado-Ado-γ-Glu-. The fatty acyl group is a $C_{14}$-20 fatty acyl group, and preferably, a $C_{14}$-20 monofatty acyl group or fatty diacid monoacyl group. In certain preferred embodiments, the fatty acyl group is a $C_{16}$ or $C_{18}$ monofatty acyl group.

The present invention provides peptides having the GLP-1/glucagon dual receptor agonistic activity, which have the following characteristics in activity by the aforementioned structural design of the present invention: the polypeptides provided in the present invention have at least 0.1% receptor agonist activity compared to natural ligands of each receptor of GLP-1R/GCGR, such as the activity expressed by $EC_{50}$ (nM) in examples of the present invention. An $EC_{50}$ (nM) value of the compounds provided in the present invention includes, but is not limited to, $10^{-2}$ to $10^{2}$ times that of an endogenous ligand (GLP-1), preferably, the active strength is equivalent to that of the endogenous ligand (GLP-1), 1-10 times, such as 2 times, 3 times, 6 times, and 10 times, weaker or stronger than that of the endogenous ligand (GLP-1), or 10-100 times stronger than that of the endogenous ligand (GLP-1). The agonist activity strength to the glucagon receptor (GCGR) is expressed by an $EC_{50}$ (nM) value, which is equivalent to that of an endogenous ligand (GC) or 1 to $10^{3}$ times that of the endogenous ligand (GC). In a preferred embodiment, the agonistic actions of the compounds of the present invention on the GLP-1 receptor are stronger than the agonistic actions on the glucagon receptor, or the agonistic actions on the two receptors are equivalent. The relative activity strength to the GLP-1 and glucagon receptors can be expressed by a potency ratio ($GLP\text{-}1R_{EC50}/GCGR_{EC50}$), that is, a GLP-1/glucagon receptor potency ratio of the polypeptide containing the sequence of the general formula I provided in the present invention includes, but is not limited to, 10:1 to 1:100. In a preferred embodiment of the present invention, the ratio is in a range of 10:1 to 1:10, and more preferably, in a range of 5:1 to 1:10.

A basic peptide chain of the polypeptide derivatives having the sequence of the general formula I provided in the present invention can be prepared by methods well-known in the art:

1) synthesizing in a stepwise manner by a conventional solid phase or liquid phase method or by fragment assembly;
2) expressing a nucleic acid construct for encoding a polypeptide in host cells, and collecting an expression product from a host cell culture;
3) affecting a cell-free in vitro expression of a nucleic acid construct for encoding a polypeptide, and collecting an expression product; or obtaining peptide fragments by any combination of methods 1), 2), and 3), and then linking these fragments to obtain the target peptide.

In a preferred embodiment of the present invention, the target peptide is prepared by an Fmoc solid phase synthesis method, which is well known by those skilled in the art.

Substituent groups can be introduced stepwise synthetically by the above peptide synthesis steps. Substituents with appropriate protecting groups are used, such as Fmoc-8-amino-3,6-dioxaoctanoic acid and Fmoc-γ-Glu-OtBu. Introduction of a fatty chain moiety, especially a fatty diacid monoacyl group, can be realized by using, but not limited to, $C_{18}$ or $C_{20}$ mono-tert-butyl alkanoate. After each coupling step, an unreacted intermediate can be blocked with excessive acetic anhydride and pyridine. ε-amino group of a modifiable Lys can be protected by Mtt or Dde.

Purification: after conjugation reaction, the target product can be separated by an appropriate method well known in the field. The appropriate method includes, but is not limited to, ultrafiltration, dialysis, chromatography, etc. In a preferred embodiment of the present invention, the target product is purified by preparative high performance liquid chromatography.

Receptor activity assay: in an embodiment of the present invention, the activity of the polypeptides on the GLP-1/GC receptors is assessed by effects on GLP-1/GC receptor-mediated cAMP production in vitro.

Regulatory effects on body weight and blood glucose: in an embodiment of the present invention, effects of the polypeptides provided in the present invention on body weight and blood glucose are assessed by single dose administration to glucose loaded normal mouse models and successive administration to high-fat diet obese diabetes (Dio) mouse models.

Experimental results of the present invention show that the activities of the compounds provided by the technical solutions of the present invention on the GLP-1 receptor (GLP-1R) are equivalent to that of endogenous GLP-1, the compounds retain a certain activity on the GC receptor, with a potency ratio within an appropriate range. Compared with GLP-1 receptor mono agonist, the compounds provided by the technical solutions of the present invention can effectively reduce blood glucose while promoting weight loss and preventing weight gain more significantly, can reverse or alleviate hepatic steatosis and insulin resistance, and show multiple unexpected benefits for complex metabolic syndrome.

BRIEF DESCRIPTION OF THE DRAWINGS

Hereinafter, embodiments of the present invention will be described in detail below with reference to the drawings, among which:

FIG. 2 shows effects of compounds dgc005, dgc016 and dgc020 on hepatic lesions in DIO model mice after 23 days of successive administration, wherein FIG. 2A shows the pathological examination image of liver section of blank control group, FIG. 2B shows the pathological examination image of liver section of model control group, FIG. 2C shows the pathological examination image of liver section of positive control drug group, FIG. 2D shows the pathological examination image of liver section of compound dgc005 group, FIG. 2E shows the pathological examination image of liver section of compound dgc016 group, and FIG. 2F shows the pathological examination image of liver section of compound dgc020 group;

DETAILED DESCRIPTION OF THE INVENTION

Figure 1:
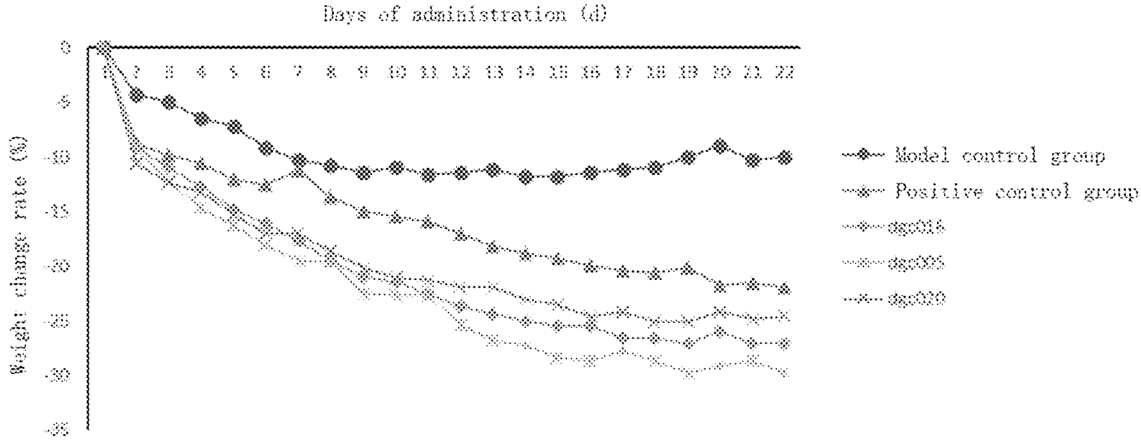
FIG. 1 shows effects of compounds dgc016, dgc005 and dgc020 on body weights of DIO mice.

The present invention is further described below in conjunction with specific examples. The examples are only illustrative of the present invention, and are not to be construed as limiting the present invention in any manner.

Description of Abbreviations for Amino Acids:

Gly: glycine (G)
Ala: alanine (A)
Val: valine (V)
Leu: leucine (L)
Phe: phenylalanine (F)
Trp: tryptophan (W)
Ser: serine (S)
Thr: threonine (T)
Glu: glutamic acid (E)
Gln: glutamine (Q)
Asp: aspartic acid (D)
Asn: asparagine (N)
Tyr: tyrosine (Y)
Arg: arginine (R)
Lys: lysine (K)
His: histidine (H)
Aib: α-aminoisobutyric acid
Ado: 8-amino-3,6-dioxaoctanoic acid Description of abbreviations for reagents Boc: tert-butoxycarbonyl
Tert-Bu: tert-butyl
DCM: dichloromethane
DIC: diisopropylcarbodiimide
Fmoc: 9-fluorenylmethoxycarbonyl
HoBt: 1-hydroxybenzotriazole
HBTU: 2-(1H-benzotriazole-1-yl)-1,1,3,3-tetramethyl-uronium hexafluorophosphate
HATU: O-(7-azabenzotriazol-1-yl)-N,N,N',N'-tetramethyl-uronium
hexafluorophosphate
Mtt: 4-methyltriphenylmethyl
NMP: N-methylpyrrolidone
DMF: dimethylformamide
Pbf: 2,2,4,6,7-pentamethyldihydrobenzofuran
Dde: 1-(4,4-dimethyl-2,6-dioxocyclohexylidene)-3-methyl-butyl
Trt: triphenylmethyl
EDT: ethanedithiol
TFA: trifluoroacetic acid
TIS: triisopropylsilane
FBS: fetal bovine serum

Example 1

A basic linear sequence of a polypeptide and a derived peptide with a modified side chain of the present invention were prepared by the following general methods.

1) Synthesis: the polypeptide was synthesized based on an Fmoc strategy by using a PSI200 polypeptide synthesizer according to the following steps:

a) In the presence of an activator system, a resin solid phase carrier was coupled to an Fmoc-protected C-terminal amino acid to yield Fmoc-amino acid-resin, wherein the polypeptide with the amidated C terminus was synthesized by using an amino resin such as Rink Amide AM, Rink Amide, and Rink MBHA; a ratio (mol/mol) of the Fmoc-amino acid to the resin was (3-5): 1, and the coupling activator was HOBT/DIC or HOB T/HBTU/DIEA.

b) Extension of the peptide chain: amino acids were assembled according to an amino acid sequence of the peptide by solid phase synthesis method to obtain a peptide-resin conjugate with protected N terminus and side chain, wherein amino acids with side chains were protected as follows: tryptophan was protected with Boc, glutamic acid was protected with OtBu, lysine was protected with Boc, glutamine was protected with Trt, tyrosine was protected with tBu, serine was protected with Trt or tBu, aspartic acid was protected with OtBu, threonine was protected with tBu, cysteine was protected with Trt, arginine was protected with Pbf, an α-amino group of histidine was protected with Boc, the side chain of histidine was protected with Trt or Boc, and the modifiable ε-amino group of lysine was protected with Dde. Coupling activator used was HOBT/DIC, HOBT/HATU/DIEA or HOBT/HATU/DIEA, the reaction endpoint was monitored by ninhydrin method, and deprotection agent was 20% piperidine in NMP (DMF).

c) Deprotection of the ε-amino group of lysine:

the fully protected polypeptide-resin synthesized in the previous step was washed three times with NMP-DCM (1:1 (v/v)), then the newly prepared 2.0% hydrazine hydrate in NMP was added, the mixture was stirred at the room temperature for 12 min and filtered, the previous operation was repeated twice, and the resin was washed for three times with DCM and NMP, respectively.

d) Modification of the side chain of lysine:

After the ε-amino group of lysine was deprotected, Fmoc-Ado or Fmoc-γ-Glu (tBu) and HOBt/HBTU, DIEA were added in a ratio (resin:linking group=1: (4-5) (mol/mol)), and stirred to react for 2.0-4.0 h, then Fmoc was deprotected, and a linker arm and a fatty acyl group of the desired chain length were continued to be linked by the same method. If the reaction was still not completed after the previous operation was repeated twice, excessive acetic anhydride/pyridine was added to block and the reaction was continued to the next step.

e) Cleavage of the polypeptide: the fully protected peptide-resin was first washed with NMP and then washed three to six times with DCM to remove NMP, a TFA/EDT/TIS/H2O (92.5:2.5:2.5:2.5 (v/v)) solution was added, and the mixture was stirred under the protection of nitrogen gas at the room temperature for 90 min to deprotect and de-resin. The mixture was filtered by suction to obtain a filtrate, crude polypeptide was precipitated with excessive ice ethyl ether, centrifuged, and the precipitates were collected, washed with a small amount of ethyl ether, and dried under vacuum to obtain crude polypeptide product.

2) Purification: the crude polypeptide product was dissolved in water or 10-15% acetonitrile (10-50 mg/mL), separated and purified by preparative HPLC using a C8 or C18 chromatographic column with acetonitrile-water-trifluoroacetic acid system, concentrated, and lyophilized to obtain pure polypeptide product (purity ≥97%).

Polypeptide derivatives with the following structures shown in Table 1 were prepared by the above mentioned method and confirmed by mass spectrometry.

TABLE 1

Synthesized compounds

| Compound No. | Sequence No. | K* |
|---|---|---|
| dgc001 | SEQ ID NO. 4 | -γE-$OC_{16}H_{31}$ |
| dgc002 | SEQ ID NO. 6 | -Ado-Ado-γE-$OC_{17}H_{32}COOH$ |
| dgc003 | SEQ ID NO. 7 | -γE-$OC_{16}H_{31}$ |
| dgc004 | SEQ ID NO. 8 | -γE-$OC_{16}H_{31}$ |
| dgc005 | SEQ ID NO. 8 | -γE-γE-$OC_{16}H_{31}$ |
| dgc006 | SEQ ID NO. 8 | -Ado-Ado-γE-$OC_{17}H_{31}COOH$ |
| dgc007 | SEQ ID NO. 12 | -γE-$OC_{16}H_{31}$ |
| dgc008 | SEQ ID NO. 13 | -γE-$OC_{16}H_{31}$ |
| dgc009 | SEQ ID NO. 13 | -Ado-Ado-γE-$OC_{16}H_{31}$ |
| dgc010 | SEQ ID NO. 13 | -γE-γE-$OC_{16}H_{31}$ |
| dgc011 | SEQ ID NO. 8 | -Ado-Ado-γE-$OC_{16}H_{31}$ |
| dgc012 | SEQ ID NO. 17 | -Ado-Ado-γE-$OC_{17}H_{32}COOH$ |
| dgc013 | SEQ ID NO. 18 | -γE-γE-$OC_{16}H_{31}$ |
| dgc014 | SEQ ID NO. 18 | -γE-$OC_{16}H_{31}$ |
| dgc015 | SEQ ID NO. 19 | -γE-$OC_{16}H_{31}$ |
| dgc016 | SEQ ID NO. 19 | -γE-γE-$OC_{16}H_{31}$ |
| dgc017 | SEQ ID NO. 21 | -γE-$OC_{16}H_{31}$ |
| dgc018 | SEQ ID NO. 24 | -γE-$OC_{16}H_{31}$ |
| dgc019 | SEQ ID NO. 25 | -γE-$OC_{16}H_{31}$ |
| dgc020 | SEQ ID NO. 25 | -γE-γE-$OC_{16}H_{31}$ |
| dgc021 | SEQ ID NO. 25 | -Ado-Ado-γE-$OC_{16}H_{31}$ |
| dgc022 | SEQ ID NO. 27 | -γE-$OC_{16}H_{31}$ |

Note:
the C-terminal carboxyl group of each compound was amidated.

Example 2 Action on GLP-1/GC Receptors

The activities of the polypeptides on GLP-1/GC receptors were assessed by effects on GLP-1/GC receptor-mediated cAMP production in vitro.

HEK293 cell line stably expressing GLP-1R or GCGR was used for screening GLP-1R and GCGR agonist.

Preparation of test sample: each compound was prepared into 100 μM stock solution, and then gradually diluted to working concentrations of 1 μM, 100 nM, 10 nM, 1 nM, $10^{-1}$ nM, $10^{-2}$ nM, $10^{-3}$ nM, and $H_2O$.

Preparation of Positive Control Solution:

GLP-1:

Storage method: GLP-1 was dissolved in 0.1% BSA in ultrapure water to obtain 1 mM stock solution, and sealed and stored at −80° C.

Working concentrations: 1 μM, 100 nM, 10 nM, 1 nM, $10^{-1}$ nM, $10^{-2}$ nM, $10^{-3}$ nM, and $H_2O$ (0.1% BSA was contained in each well).

Glucagon (GC):

Storage method: GC was dissolved in DMSO to obtain a 1 mM stock solution, and sealed and stored at −80° C.

Working concentrations: 1 μM, 100 nM, 10 nM, 1 nM, $10^{-1}$ nM, $10^{-2}$ nM, $10^{-3}$ nM, and DMSO (1% DMSO was contained in each well).

Reagents and Instruments:

Main reagents: DMEM (GIBCO, Cat No: 12800017); and cAMP assay kit (PerkinElmer, Cat No: TRF0264).

Main instruments: Envision 2104 multifunctional microplate reader (PerkinElmer).

Experimental Procedure:

1) Each compound to be tested was mixed with a serum-free medium (containing 0.1% BSA and 0.5 mM IBMX) to obtain a solution at a concentration 2 times the working concentration.

2) The cells were digested, suspended in a serum-free medium (containing 0.5 mM IBMX), counted, and placed in a 384-well plate at a density of 1,000 cells/5 μL/well, then 5 μL of the testing compound was added, and the plate was placed in dark for reaction for 30 min.

3) After the reaction was completed, a substrate for detecting cAMP was added, and the plate was placed in dark for reaction at the room temperature for 60 min.

4) After the reaction was completed, the plate was placed on the Envision2104 multifunctional microplate reader for detection, and the ratio of optical density (OD) values at 665 nm and 615 nm were read out.

5) 50% effective concentrations ($EC_{50}$) were calculated by using the Origin software.

TABLE 2

| Agonistic activity of polypeptides on GLP-1/GC receptors | | | |
|---|---|---|---|
| Compound | GLP-1R (nM $EC_{50}$) | GCGR (nM $EC_{50}$) | Potency ratio ($GLP\text{-}1R_{EC50}/GCGR_{EC50}$) |
| GLP-1 | 0.5614 | >100 | — |
| Glucagon (GC) | >100 | 0.0499 | — |
| dgc001 | 1.127 | 0.806 | 1.40:1 |
| dgc003 | 0.291 | 1.038 | 1:3.57 |
| dgc004 | 0.113 | 5.842 | 1:51.6 |
| dgc005 | 0.484 | 1.157 | 1:2.39 |
| dgc006 | 0.472 | 6.413 | 1:13.59 |
| dgc007 | 0.280 | 0.971 | 1:3.47 |
| dgc008 | 0.742 | 2.029 | 1:2.73 |
| dgc009 | 0.092 | 8.220 | 1:89.35 |
| dgc010 | 0.537 | 0.614 | 1:1.14 |
| dgc011 | 0.955 | 4.131 | 1:4.33 |
| dgc012 | 0.044 | 2.175 | 1:49.43 |
| dgc013 | 0.319 | 1.990 | 1:6.24 |
| dgc014 | 0.516 | 0.821 | 1:1.59 |
| dgc015 | 0.899 | 1.528 | 1:1.70 |
| dgc016 | 1.229 | 0.342 | 3.59:1 |
| dgc017 | 0.627 | 3.951 | 1:6.30 |
| dgc018 | 0.401 | 1.301 | 1:3.24 |
| dgc019 | 0.792 | 1.826 | 1:2.31 |
| dgc020 | 1.511 | 0.883 | 1.71:1 |
| dgc021 | 0.382 | 3.932 | 1:10.29 |

The in vitro receptor agonist activity results in Table 2 show that the polypeptide derivatives having the amino acid sequences of the present invention have the dual agonist activity to the GLP-1/GC receptors, and the potency ratios of the polypeptide derivatives are in an appropriate range.

Example 3 Hypoglycemic Action of Compounds of Example 1

The hypoglycemic action of each compound of Example 1 was assessed by a glucose loading test on normal mice after single administration.

Method: Kunming mice (male, with a weight of 20-22 g) were acclimated in a barrier environment animal room for 3 days, divided into a blank control group, a model control group, a positive control group, and test compound groups, 5 mice in each group, and fasted for 6 h. Saline was administered to each mouse in the blank control group and the model control group, the compounds and a positive control drug were respectively administered to each mouse in the test compound groups and the positive control group at a dose of 30 nmol/kg, and the positive control drug was semaglutide. 60 min after administration, glucose was intragastrically administered to each mouse in the model control group, the positive control group, and the test compound groups at a dose of 2.5 g/kg (0.01 $mL \cdot g^{-1}$ weight), distilled water was administered to each mouse in the blank control group, and blood glucose levels were determined 30 min after glucose loading. Results are shown in Table 3.

TABLE 3

| Effects of compounds on glycemic loads in normal mice (n = 5, mmol/L) | | | |
|---|---|---|---|
| Group | Fasting blood glucose level | Blood glucose level after glucose loading | Blood glucose reduction rate (%) |
| Blank control group | 4.08 ± 0.83 | 4.48 ± 0.83 | — |
| Model control group | 3.43 ± 0.66 | 17.00 ± 2.96 | — |
| Positive control group | 3.78 ± 1.28 | 5.58 ± 1.55** | 67.18 |
| dgc005 | 3.96 ± 0.62 | 6.70 ± 1.88** | 60.59 |
| dgc016 | 3.66 ± 0.77 | 6.82 ± 1.78** | 59.88 |
| dgc020 | 4.24 ± 0.63 | 9.82 ± 2.06**## | 42.24 |
| dgc003 | 4.20 ± 0.97 | 8.82 ± 1.63**# | 48.12 |
| dgc004 | 3.42 ± 0.85 | 8.46 ± 2.28**# | 50.24 |
| dgc013 | 3.92 ± 0.51 | 9.26 ± 1.76**## | 45.53 |
| dgc010 | 3.78 ± 0.84 | 8.10 ± 1.13**# | 52.35 |
| dgc017 | 3.72 ± 0.37 | 10.36 ± 1.87**## | 39.06 |
| dgc006 | 3.80 ± 0.51 | 8.02 ± 2.92** | 52.82 |
| dgc008 | 3.64 ± 1.00 | 8.72 ± 1.99**# | 48.70 |

**P < 0.01 when compared to the model control group;
P < 0.01 when compared to the positive control group; and
#P < 0.05 when compared to the positive control group The results show that compared with the model control group, the test compounds at the administration dose can significantly (P<0.01) inhibit the rise of blood glucose in the normal mice after glucose loading, and the inhibitory action of the compound dgc005, dgc016 or dgc006 is equivalent to that of the positive control drug.

Example 4

Therapeutic action of compounds dgc005, dgc016, and dgc020 on obese model mice after multiple administrations Experimental Method:

C57BL/6J Gpt mice (purchased from GemPharmatech (Jiangsu) Co., Ltd.) (6-8-week-old) were fed with H10060 high-fat diet (purchased from Beijing HFK Bioscience Co., Ltd.) to obtain diet-induced obesity (DIO) models, mice in a blank control group (n=5) were fed with standard diets, and all the mice were fed for 11 weeks after being purchased. One day before the first administration, the mice in the model group were randomly divided into 5 groups according to their weights (within a range of 39.5-49.5 g), i.e., a model control group, a positive control group, and test compound groups (dgc005, dgc016, and dgc020), respectively, 5 mice in each group, which were administered every day by subcutaneous injection. Saline was subcutaneously injected in the blank control group and the model control group every day. The administration was performed for 23 days. The positive control drug and the test compounds were administered at a dose of 30 nmol/kg, and the administration volume for each group was 0.005 mL/g weight. The mice were weighed before each administration, and 72-h food intake was weighed every three days. The mice fasted for 16 h before the last administration, fasting blood glucose levels were determined, blood was sampled from the orbital venous plexus to determine triglycerides and total cholesterol, and the liver was taken out for pathological section observation.

Results:

1. Effects on the weight: see FIG. 1. From day 3 of administration, there is a significant difference between each test compound and the positive control drug in weight loss, and shows constant decrease of body weight. Compared to day 1 of administration, weight decreasing rates of the test compounds dgc005, dgc016, and dgc020 without fasting before the last administration are 27%, 29.3%, and 25.0%, respectively, and the weight decreasing rate of the positive control drug is 20.9%. It indicates that the weight reduction action of each test compound at the administration dose is better than that of the positive control drug.

2. Effects on fasting blood glucose after multiple administrations: see Table 4.

TABLE 4

Effects of compounds on fasting blood glucose in animals after 23 days of successive administration (n = 5)

| | Blank control group | Model control group | Positive control group | dgc005 | dgc016 | dgc020 |
|---|---|---|---|---|---|---|
| Fasting blood glucose (mmol/L) before the last administration | 4.46 ± 0.27 | 6.40 ± 0.80 ΔΔ | 4.48 ± 0.84 ** | 4.60 ± 0.34 ** | 4.18 ± 0.40 ** | 4.78 ± 0.46 ** |

**P < 0.01 when compared to the model control group
#: P < 0.05 when compared to the positive control group
ΔΔP < 0.01 when compared to the blank control group The results in Table 4 show that the improvement action of each test compound after 23 days of successive administration on fasting blood glucose is equivalent to that of the positive control drug.

3. Effects on food intake: see results in Table 5. 72-h food intake of each test compound group decreases to an extent compared to that of the model control group, and 72-h food intake shows a gradual increasing trend from day 7.

TABLE 5

Effects on 72-h food intake of animals after multiple administrations (g/mouse, n = 5)

| Days of administration | Blank control group | Model control group | Positive control group | dgc005 | dgc016 | dgc020 |
|---|---|---|---|---|---|---|
| 4 | 11.30 | 5.60 | 3.50 | 2.50 | 3.30 | 3.50 |
| 7 | 9.30 | 6.00 | 5.80 | 3.80 | 4.80 | 4.50 |
| 10 | 10.40 | 8.20 | 5.40 | 4.20 | 6.10 | 5.70 |
| 13 | 9.20 | 7.80 | 5.50 | 4.60 | 5.70 | 5.50 |

4. Effects on blood fat: see results in Table 6. The compound dgc005 reduced total cholesterol (TC) in a certain extent (P<0.05 when compared to the model control group, P<0.05 when compared to the positive control group, and no statistical difference when compared to the blank control group), and can significantly reduce triglycerides (TGs) (P<0.01 when compared to the model control group, P<0.05 when compared to the positive control group, and P<0.01 when compared to the blank control group). The compound dgc016 has a triglyceride reduction action (P<0.01 when compared to the model control group, no statistical difference when compared to the positive control group, and P<0.01 when compared to the blank control group).

TABLE 6

Effects of test compounds on blood fat in animals after 23 days of multiple administrations (mmol/L, n = 5)

| | Blank control group | Model control group | Positive control group | dgc005 | dgc016 | dgc020 |
|---|---|---|---|---|---|---|
| TC | 3.11 ± 0.24 | 3.95 ± 0.52Δ | 3.97 ± 0.52Δ | 3.07 ± 0.50*# | 3.32 ± 0.73 | 3.62 ± 0.84 |
| TG | 1.35 ± 0.08 | 1.21 ± 0.14 | 0.90 ± 0.13**ΔΔ | 0.58 ± 0.10**#ΔΔ | 0.75 ± 0.10**ΔΔ | 0.88 ± 0.28Δ |

**P < 0.01 when compared to the model control group; and
*P < 0.05 when compared to the model control group
#P < 0.05 when compared to the positive control group
ΔΔP < 0.01 when compared to the blank control group; and
ΔP < 0.05 when compared to the blank control group 5. Examination of Liver Pathological Section:

The liver of each C576L/6 mouse in the groups was fixed with 12% formaldehyde and prepared into a specimen, and the tissue block was repaired, dehydrated with graded alcohol, embedded in paraffin, stained with HE, and examined under a light microscope.

Figure 2:
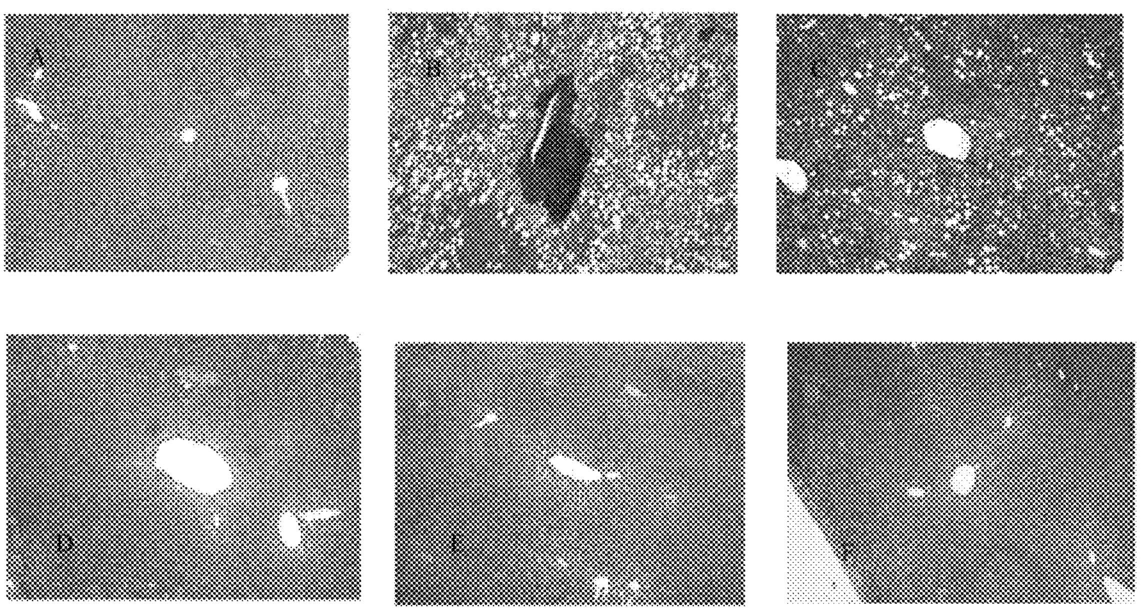

Results:

Blank control group: the hepatic lobules of 2 animals are structurally intact, hepatic cords are arranged neatly, the morphology of hepatocytes is clear, and no obvious pathological changes are seen in portal areas and interstitium (see FIG. 2A).

Model control group: severe lesions can be seen in 2 animals: diffused vacuolar degeneration of hepatocytes, and infiltration of some perivascular mononuclear cells (2/2, severe) (see FIG. 2B).

Positive control drug group: mild to moderate lesions can be seen in 2 animals: vacuolar degeneration of few to many hepatocytes, and infiltration of some perivascular mononuclear cells and local transparent hepatocyte foci in 1 animal (½, mild, and ½, moderate) (see FIG. 2C).

Compound dgc005 group: the hepatic lobules of 2 animals are structurally intact, hepatic cords are arranged neatly, the morphology of hepatocytes is clear, and no obvious pathological changes are seen in portal areas and interstitium (see FIG. 2D).

Compound dgc016 group: the hepatic lobules of 2 animals are structurally intact, hepatic cords are arranged neatly, the morphology of hepatocytes is clear, and no obvious pathological changes are seen in portal areas and interstitium (see FIG. 2E).

Compound dgc020 group: the hepatic lobules of 2 animals are structurally intact, hepatic cords are arranged neatly, the morphology of hepatocytes is clear, and no obvious pathological changes are seen in portal areas and interstitium (see FIG. 2F).

Conclusions:

It can be seen from the microscopic examination results that compared with the blank control group, different degrees of vacuolar degeneration of hepatocytes and infiltration of some perivascular mononuclear cells can be seen in the liver of each mouse in the model control group of the experiment, and the lesions are severe; the above lesions can also be seen in the liver of each mouse in the positive control drug group, and degrees of the lesions are significantly reduced to mild to moderate, which indicates that the positive control drug has a certain therapeutic effect on the liver lesions in the models. In the test compound groups of the present invention, the hepatic lobules of each mouse are structurally intact, hepatic cords are arranged neatly, the morphology of hepatocytes is clear, no obvious pathological changes are seen in portal areas and interstitium, and there is no difference between each test compound group and the blank control group, which indicates that the test compounds of the present invention have significant therapeutic effects on the liver lesions in the models.

Example 5

Effects of Compounds Dgc003, Dgc004, Dgc010, and Dgc017 on Weights of DIO Model Mice after 2 Weeks of Administration Method: C57BL/6N mice were fed with H10060 high-fat diets to obtain diet-induced obesity (DIO) models, and mice in a control group (n=5) were fed with standard diets. One day before the first administration, the mice in the model group were randomly divided into 6 groups according to their weights (within a range of 40.5-50.5 g), i.e., a model control group, a positive control group, and test compound groups (dgc003, dgc004, dgc010, and dgc017), respectively, 5 mice in each group, which were administered once a day by subcutaneous injection. Saline was subcutaneously injected into each mouse in the blank control group and the model control group every day. The administration was performed for 14 days. The positive control drug and the test compounds were administered at a dose of 30 nmol/kg, and the administration volume for each group was 0.005 mL/g weight. The mice were weighed before each administration, and 72-h food intake was weighed every three days.

Figure 3:
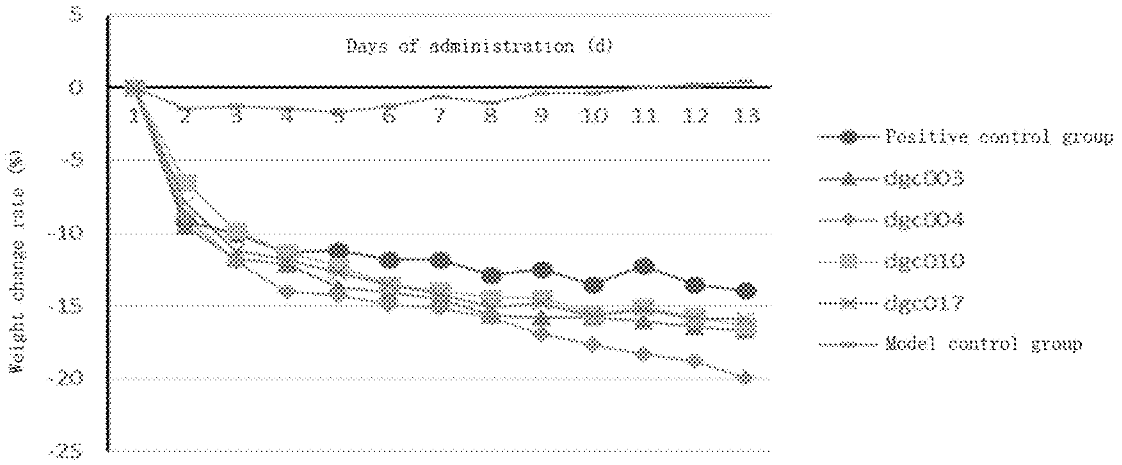
FIG. 3 shows effects of compounds dgc003, dgc004, dgc010 and dgc017 on weights of DIO model mice after 13 days of successive administration.

Results: see FIG. 3. During 2 weeks of successive administration, the weight decreases significantly after 1 to 5 days of positive control drug administration, and then the downward trend levels off; and there is a significant difference between each test compound group and the positive control drug group in the decreasing rate after 5 days of administration, the weight of each mouse in the test compound groups shows a continuous decreasing trend, decreasing rates of the dgc003, dgc004, dgc010, and dgc017 groups by the last administration are 16.7%, 19.9%, 16.4%, and 15.9%, respectively, which are all greater than 12.9% of the positive control drug group.

Example 6

Effects of Compounds Dgc005 and Dgc016 on Weights and Blood Glucose of DIO Mice after Multiple Administrations at Different Doses Method:

40 C57BL/6N mice were purchased from Beijing Vital River Laboratory Animal Technology Co., Ltd. Mice in a model group (n=35) were fed with H10060 high-fat diets to obtain diet-induced obesity (DIO) models, mice in a blank control group (n=5) were fed with standard diets, and all the mice were fed for 36 weeks. On the day of the first administration, the mice in the model group were randomly divided into 7 groups according to their weights (within a range of 45-60 g), i.e., a model control group, positive control groups (semaglutide at doses of 10 nmol/kg and 30 nmol/kg, respectively), and test compound groups (dgc005 and dgc016 at doses of 10 nmol/kg and 30 nmol/kg, respectively), 5 mice in each group. The positive control drug and the test compounds were respectively subcutaneously injected into each mouse in the positive control groups and the test compound groups every day, saline was subcutaneously injected into each mouse in the blank control group and the model control group, and the administration was performed for 22 days (the administration volume for each group was 0.005 mL/g weight). The mice were weighed before each administration, and 72-h food intake was weighed every three days. The mice fasted for 16 h before the last administration, and 30 min after administration, a glucose solution (1 g/kg, the administration volume was 0.01 mL/g weight) was intragastrically administered to each mouse for glucose tolerance test. Blood glucose levels were determined 0.5 h after glucose loading.

Figure 4:
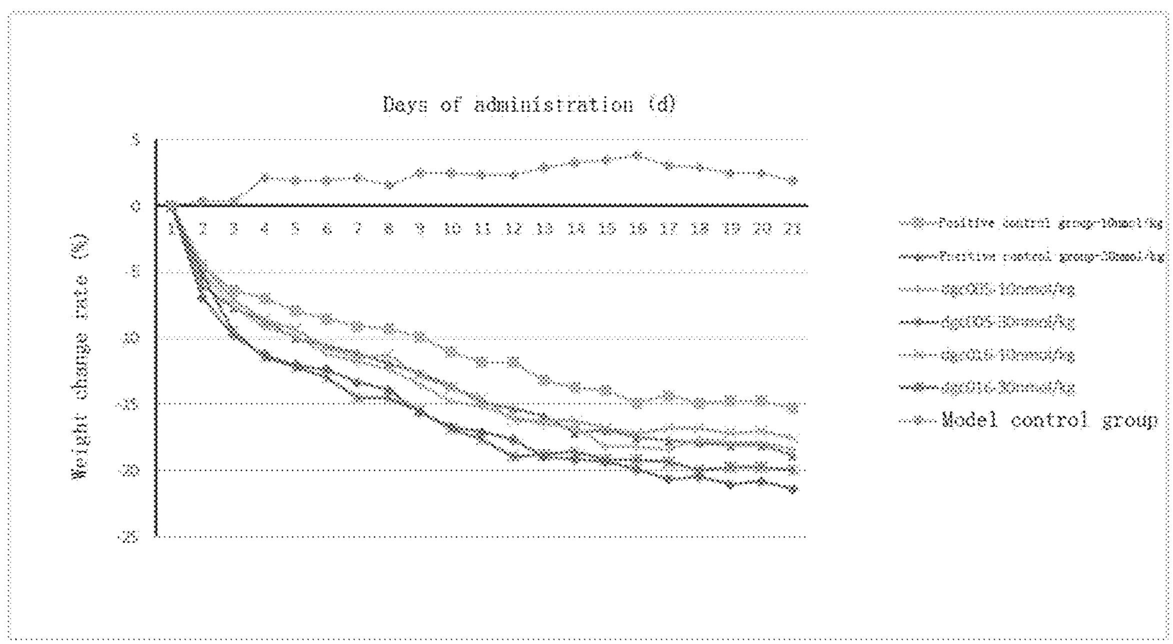
FIG. 4 shows effects of compounds dgc005 and dgc016 on weights of DIO model mice after 21 days of successive administration at different doses.

Results:

1) Effects on the weight: see results in FIG. 4. Compared with the model control group, weights of the mice in the positive control groups and the test compound groups continuously decrease from day 2 of administration. There is a significant difference between each high-dose test compound group and the positive control group in the decreasing rate from day 3, and there is a significant difference between each low-dose test compound group and the positive control group in the decreasing rate from day 4. The weight decreasing rate of each test compound group at each dose without fasting on day 21 of administration is greater than that of the positive control group at corresponding dose. Results are shown in Table 7.

TABLE 7

| Reduction rates of weights of animals without fasting in groups on day 21 of administration compared to weights on day 0 (%, n = 5) | | | | | | | | |
|---|---|---|---|---|---|---|---|---|
| Days of administration | Blank control group | Model control group | Positive control - 10 nmol/kg | Positive control - 30 nmol/kg | dgc005 - 10 nmol/kg | dgc005 - 30 nmol/kg | dgc016 - 10 nmol/kg | dgc016 - 30 nmol/kg |
| 21 | 1.63 | 1.92 | 15.28 | 18.83 | 18.41 | 21.39 | 17.56 | 19.92 |

2) Effects on Blood Glucose

Before the last administration, each test compound at each dose can significantly reduce fasting blood glucose levels in the animals before administration, and 0.5 h after glucose loading, each test compound at each dose can significantly inhibit the rise of blood glucose in the animals after glucose loading (P<0.01 when compared to the model control group, and no statistical difference when compared to the positive control groups and the blank control group), which indicates that each test compound still has a hypoglycemic action equivalent to that of the positive control drug after long-term administration. Results are shown in Table 8.

TABLE 8

| Effects of samples on glycemic loads in animals after the last administration (Day 22) (n = 5) | | | | | | | | |
|---|---|---|---|---|---|---|---|---|
| | Blank control group | Model control group | Positive control - 10 nmol/kg | Positive control 30 nmol/kg | dgc005 - 10 nmol/kg | dgc005 - 30 nmol/kg | dgc016 - 10 nmol/kg | dgc016 - 30 nmol/kg |
| Fasting blood glucose (mmol/L) before the last administration | 5.64 ± 0.76 | 7.02 ± 0.74$^{\Delta}$ | 5.54 ± 1.11* | 5.56 ± 0.91* | 5.34 ± 1.20* | 4.22 ± 2.13* | 4.68 ± 2.12* | 5.02 ± 2.34* |
| Blood glucose level (mmol/L) 0.5 h after glucose loading | 8.30 ± 0.81 | 10.52 ± 0.75$^{\Delta\Delta}$ | 7.06 ± 1.15** | 8.20 ± 0.87** | 7.52 ± 0.77** | 7.82 ± 1.09** | 7.12 ± 0.61**$^{\Delta}$ | 7.48 ± 0.78** |
| Glycemic load reduction rate | — | — | 32.89 | 22.05 | 28.52 | 25.66 | 32.32 | 28.90 |

**P < 0.01 when compared to the model control group; and

*P < 0.05 when compared to the model control group $^{\Delta\Delta}$P < 0.01 when compared to the blank control group; and $^{\Delta}$P < 0.05 when compared to the blank control group.

The invention claimed is:

1. A polypeptide derivative, a modified derivative, or a salt thereof, comprising a polypeptide having the sequence of the following general formula I:

General Formula I
$HX^{2}QGTFTSDX^{10}SKYLX^{15}EX^{17}X^{18}AX^{20}X^{21}FX^{23}AWLEX^{28}X^{29}X^{30}$ wherein,
$X^2$ is Ser, D-Ser or Aib;
$X^{10}$ is Tyr;
$X^{15}$ is Asp or Glu;
$X^{17}$ is Arg or Lys;
$X^{18}$ is Ala;
$X^{20}$ is Lys with the side chain being modified;
$X^{21}$ is Asp or Glu;
$X^{23}$ is Val or lle;
$X^{28}$ is Ala or Ser;
$X^{29}$ is Gly;
$X^{30}$ is Gly; and
the C-terminal carboxyl group is amidated.

2. The polypeptide derivative, the modified derivative, or the salt thereof according to claim 1, wherein $X^2$ is Aib.

3. The polypeptide derivative, the modified derivative, or the salt thereof according to claim 1, comprising the amino acid sequence selected from any one of SEQ ID NO: 4 to SEQ ID NO: 15.

4. The polypeptide derivative, the modified derivative, or the salt thereof according to claim 1, wherein side chain ε-amino group at $X^{20}$ is modified by coupling to a fatty acyl group through a hydrophilic linker fragment.

5. The polypeptide derivative, the modified derivative, or the salt thereof according to claim 4, wherein the hydrophilic linker fragment is selected from fragments consisting of one or more of Glu, γGlu, Gly, and Ado (8-amino-3,6-dioxaoctanoic acid).

6. The polypeptide derivative, the modified derivative or the salt thereof according to claim 5, wherein the hydrophilic linker fragment is -γGlu-, -γGlu-γGlu-, -Glu-γGlu-, -γGlu-Gly-Gly-, -γGlu-Gly-γGlu-, -γGlu-Ado-Ado-, -Ado-Ado-γGlu- or -γGlu-Ado-Ado-γGlu-.

7. The polypeptide derivative, the modified derivative or the salt thereof according to claim 4, wherein the fatty acyl group is a $C_{14}$-20 fatty acyl group.

8. The polypeptide derivative, the modified derivative, or the salt thereof according to claim 7, wherein the fatty acyl group is a $C_{16-18}$ fatty acyl group.

9. The polypeptide derivative, the modified derivative, or the salt thereof according to claim 7, wherein the fatty acyl group is a $C_{14-20}$ monofatty acyl group or a $C_{14-20}$ fatty diacid monoacyl group.

10. A pharmaceutical composition, comprising the polypeptide derivative, the modified derivative, or the salt thereof according to claim 1, and optionally one or more pharmaceutically acceptable adjuvants.

11. A method for treating a metabolic disease, comprising administering to a patient in need thereof a therapeutically effective amount of a polypeptide derivative, a modified derivative, or a salt thereof according to claim 1, wherein the metabolic disease is selected from the grouping consisting of diabetes, obesity, fatty liver disease, and hyperlipidemia, or a combination thereof.

12. The method of claim 11, wherein the fatty liver disease is non-alcoholic fatty liver disease.

* * * * *